United States Patent [19]
Yu

[11] Patent Number: 6,068,780
[45] Date of Patent: May 30, 2000

[54] MICRO-MINIATURE GAS CHROMATOGRAPH COLUMN DISPOSED IN SILICON WAFERS

[75] Inventor: Conrad M. Yu, Antioch, Calif.

[73] Assignee: The Regents of the University of California, Oakland, Calif.

[*] Notice: This patent is subject to a terminal disclaimer.

[21] Appl. No.: 08/892,586

[22] Filed: Jul. 14, 1997

Related U.S. Application Data

[63] Continuation-in-part of application No. 08/465,068, Jun. 5, 1995, abandoned.

[51] Int. Cl.[7] .................................................. B01D 15/08
[52] U.S. Cl. ............................. 216/10; 216/24; 73/23.35
[58] Field of Search ....................... 216/10, 24; 73/23.35

[56] References Cited

U.S. PATENT DOCUMENTS

| | | | |
|---|---|---|---|
| 5,192,406 | 3/1993 | Woolley | 204/454 |
| 5,575,929 | 11/1996 | Yu | 216/10 |
| 5,583,281 | 12/1996 | Yu | 73/23.42 |
| 5,589,083 | 12/1996 | Ahn et al. | 216/24 |

*Primary Examiner*—Randy Gulakowski
*Assistant Examiner*—Shamim Ahmed
*Attorney, Agent, or Firm*—Alan H. Thompson; L. E. Carnahan

[57] ABSTRACT

A micro-miniature gas chromatograph column is fabricated by forming matching halves of a circular cross-section spiral microcapillary in two silicon wafers and then bonding the two wafers together using visual or physical alignment methods. Heating wires are deposited on the outside surfaces of each wafer in a spiral or serpentine pattern large enough in area to cover the whole microcapillary area inside the joined wafers. The visual alignment method includes etching through an alignment window in one wafer and a precision-matching alignment target in the other wafer. The two wafers are then bonded together using the window and target. The physical alignment methods include etching through vertical alignment holes in both wafers and then using pins or posts through corresponding vertical alignment holes to force precision alignment during bonding. The pins or posts may be withdrawn after curing of the bond. Once the wafers are bonded together, a solid phase of very pure silicone is injected in a solution of very pure chloroform into one end of the microcapillary. The chloroform lowers the viscosity of the silicone enough that a high pressure hypodermic needle with a thumbscrew plunger can force the solution into the whole length of the spiral microcapillary. The chloroform is then evaporated out slowly to leave the silicone behind in a deposit.

11 Claims, 7 Drawing Sheets

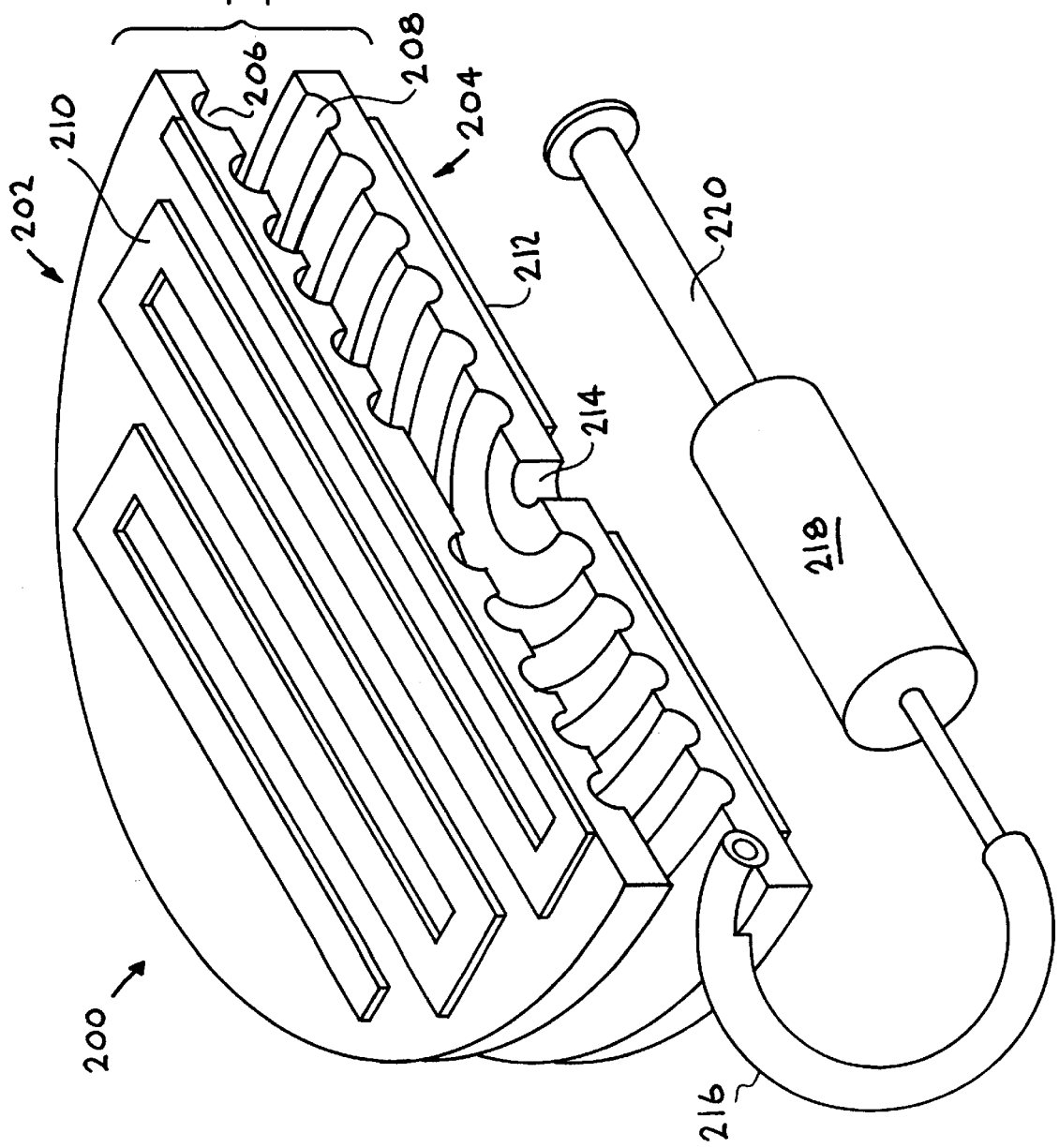

MICRO-MINIATURE GAS CHROMATOGRAPH COLUMN DISPOSED IN SILICON WAFERS

RELATED APPLICATIONS

This application is a continuation-in-part of U.S. patent application, Ser. No. 08/465,068, filed Jun. 5, 1995, now abandoded and titled, MICROCAPILLARY AND METHOD FOR BONDING SILICON WAFERS IN THE FABRICATION OF MICROCAPILLARIES. The inventors' U.S. Pat. No. 5,575,929, issued Nov. 19, 1996, and U.S. Pat. No. 5,583,281, issued Dec. 10, 1996, are incorporated herein by reference.

The United States Government has rights in this invention pursuant to Contract No. W-7405-ENG-48 between the United States Department of Energy and the University of California for the operation of Lawrence Livermore National Laboratory.

BACKGROUND OF THE INVENTION

1. Field of the Invention

The present invention relates to micro-miniature gas chromatographs and more particularly to spiral solid phase columns in silicon wafers and their fabrication.

2. Description of Related Art

Gas chromatographs are used by various scientific laboratories and government law enforcement agencies to analyze the chemical makeup of samples of materials. Some such instruments are able to reliably analyze samples where the constituents are concentrated as low as one part per million. Prior art equipment can provide useful results when as little as a few microliters of gas has been "sniffed". But such equipment is extraordinarily bulky and too delicate to be called portable.

Gas chromatographs generally comprise three basic parts, an injector, a column, and a detector. The column generally comprises a tube filled with a solid phase, through with a carrier phase must migrate. Gas samples are carried into a column by a carrier gas such as hydrogen or helium. The propagation front of the gas and how it diffuses into and back out of the column itself are highly dependent on the inside cross-sectional geometry of the column and the characteristics of the individual molecules in the gas. A circular cross-section column is ideal and produces the best results, as the lighter molecules of sample gas will diffuse faster than the heavier molecules and a circular column presents a uniform path, regardless of the direction of outward diffusion into the column walls.

The prior art has not succeeded in the fabrication of circular cross-section microcapillaries in silicon for use in GC columns. Conventional attempts to fabricate columns have resulted in squared-bottom trenches in one wafer that are capped by another wafer, typically some second, different material that produces thermal coefficient-of expansion problems.

Silicon wafers are flat and are universally processed from one side, e.g., with depositions, implants, masks and etching. Semiconductor fabrication processes are conventionally used to create non-electronic microstructures using silicon, oxides and metals.

Because of the way masks must be used with etchants, it is practically impossible to create a round tube or capillary in a single wafer of silicon. Two obstacles are encountered. First, the etching of half-round microchannels in silicon wafers has proven impossible with conventional methods. And second, bonding together matching wafers in a sandwich with the completed round capillary in between has proven to be very tedious. The conventional art in matching the geometries of features on each of the two respective halves is very precise, but the bonding together of two separate silicon wafers does not lend itself to such easy precision. Mis-registrations of even a few mils can cause ruinous overlaps of the two halves of ten to twenty percent and more.

SUMMARY OF THE INVENTION

An object of the present invention is to provide micro-miniature gas chromatograph column disposed in silicon wafers.

A further object of the present invention is to provide a method for aligning and bonding two silicon wafers with matching halves to form a whole microcapillary.

Briefly, a micro-miniature gas chromatograph column embodiment of the present invention is fabricated by forming matching halves of a circular cross-section spiral microcapillary in two silicon wafers and then bonding the two wafers together using visual or physical alignment methods. Heating wires are deposited on the outside surfaces of each wafer in a spiral or serpentine pattern large enough in area to cover the whole microcapillary area inside the joined wafers. The visual alignment method includes etching through an alignment window in one wafer and a precision-matching alignment target in the other wafer. The two wafers are then bonded together using the window and target. The physical alignment methods include etching through vertical alignment holes in both wafers and then using pins or posts through corresponding vertical alignment holes to force precision alignment during bonding. The pins or posts may be withdrawn after curing of the bond. Once the wafers are bonded together, a solid phase of very pure silicone is injected in a solution of very pure chloroform into one end of the microcapillary. The chloroform lowers the viscosity of the silicone enough that a high pressure hypodermic needle with a thumbscrew plunger can force the solution into the whole length of the spiral microcapillary. The chloroform is then evaporated out slowly to leave the silicone behind in a deposit.

An advantage of the present invention is that a method is provided for the precision joining of silicon wafers with microchannels to form microcapillaries.

Another advantage of the present invention is that a microcapillary is provided that is well formed in two bonded silicon wafers.

BRIEF DESCRIPTION OF THE DRAWINGS

FIG. 6 is an exploded assembly diagram showing two silicon wafers with spiral microcapillary halves in cross section in a micro-miniature gas chromatograph column embodiment of the present invention.

DETAILED DESCRIPTION OF THE INVENTION

Figure 1A:
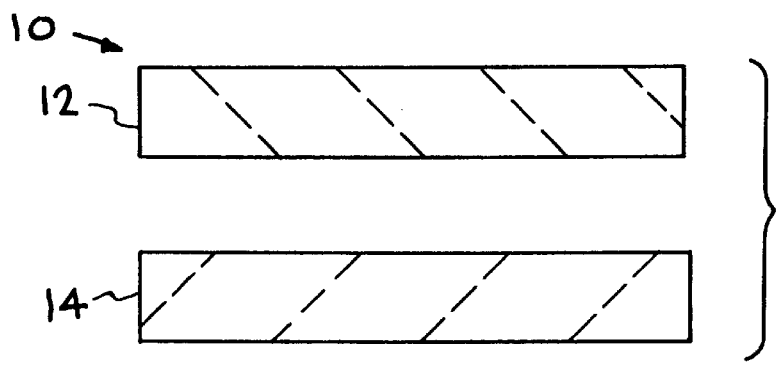
FIGS. 1A–1D are diagrams of a first method embodiment of the present invention for making a microcapillary from two silicon wafers using an alignment hole and target.
Figure 1B:
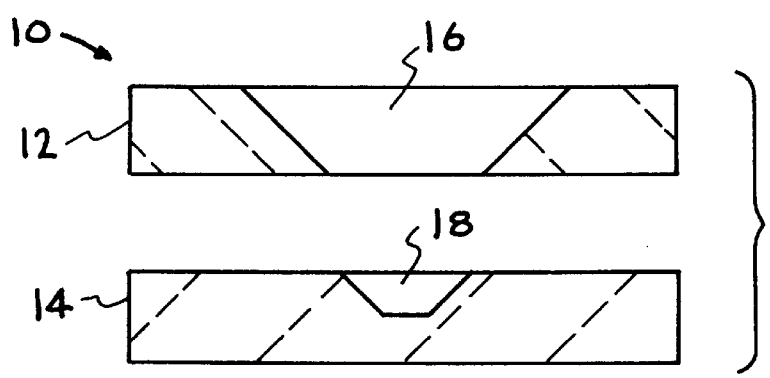
Figure 1C:
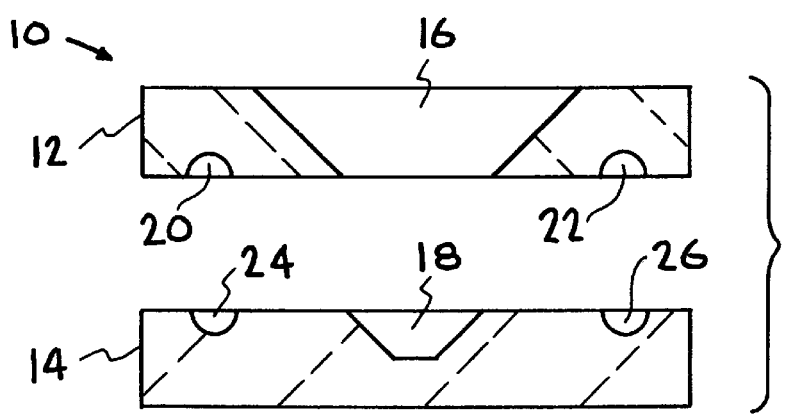
Figure 1D:
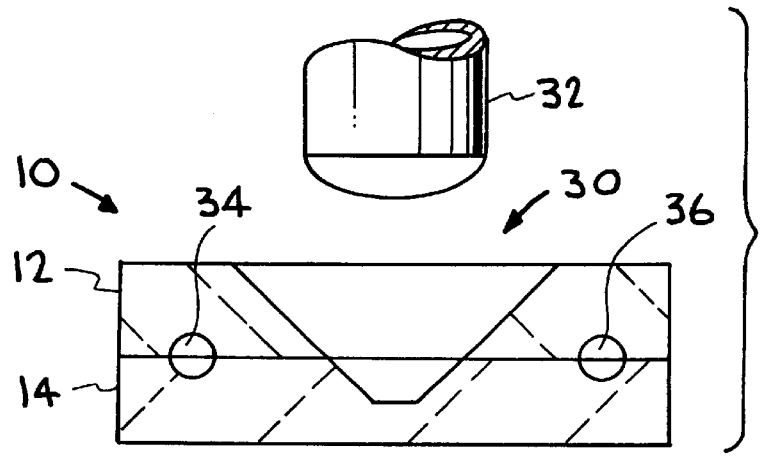
Figure 2A:
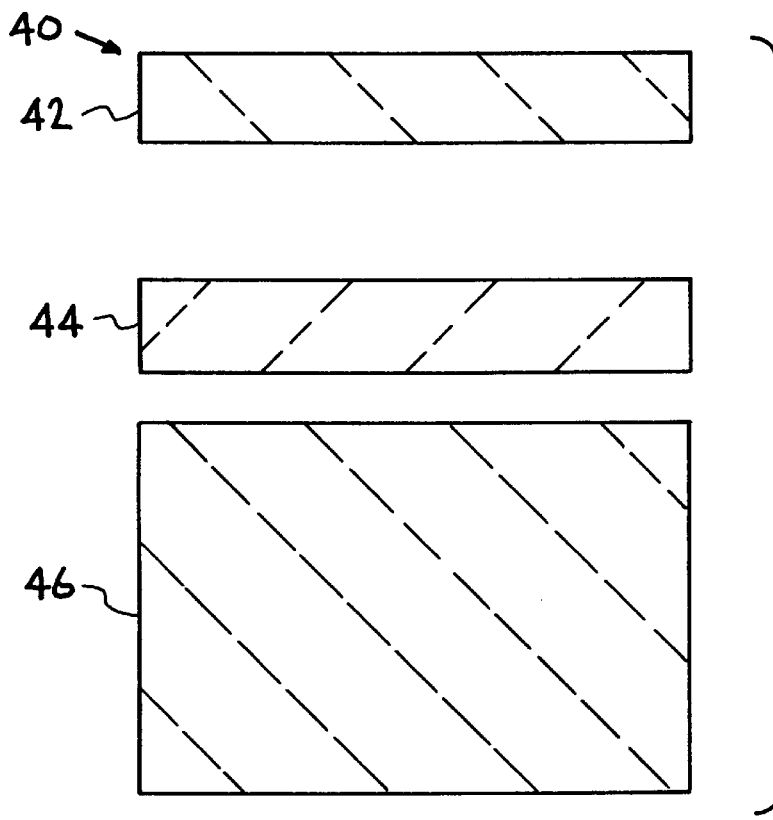
FIGS. 2A–2D are diagrams of a second method embodiment of the present invention for making a microcapillary from two silicon wafers using alignment holes and a post.
Figure 2B:
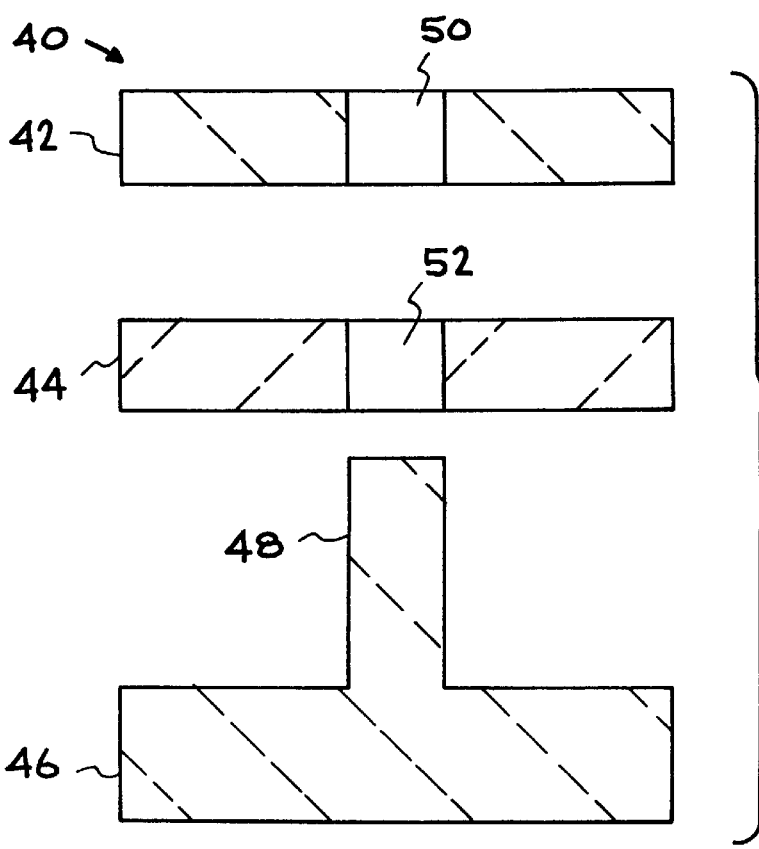
Figure 2C:
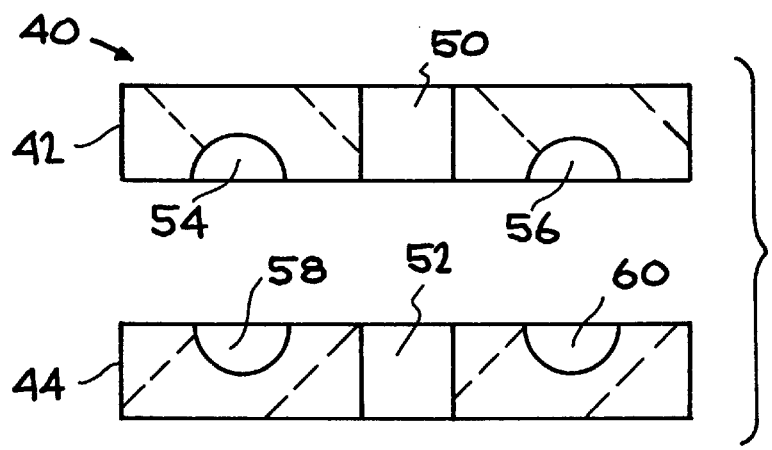
Figure 2D:
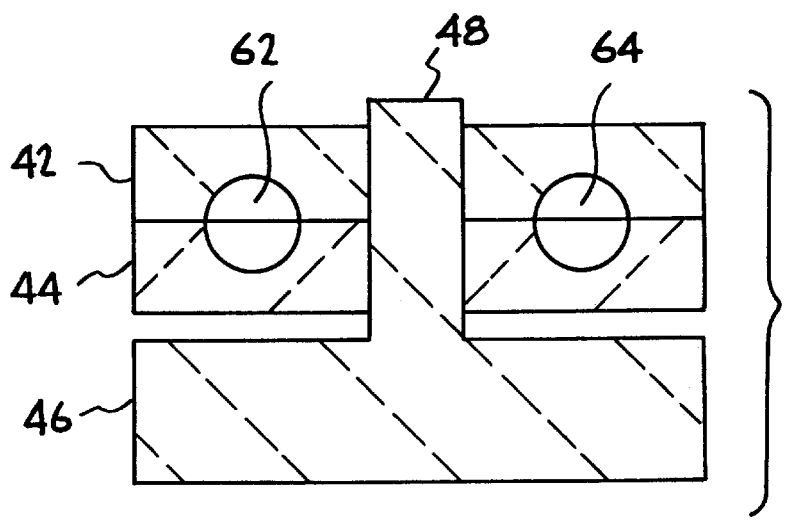
Figure 3A:
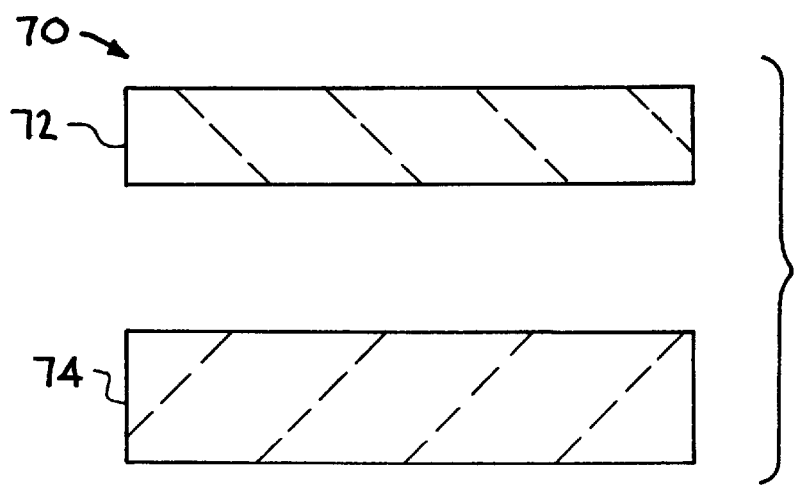
FIGS. 3A–3D are diagrams of a third method embodiment of the present invention for making a microcapillary from two silicon wafers using an alignment cavity and post.
Figure 3B:
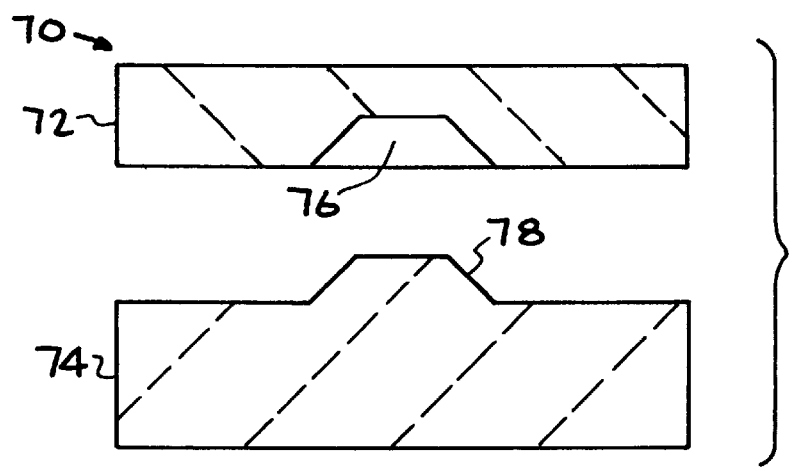
Figure 3C:
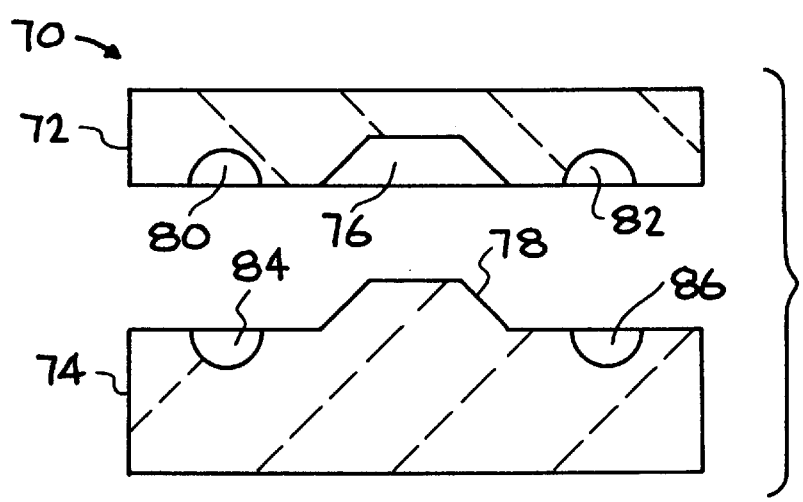
Figure 3D:
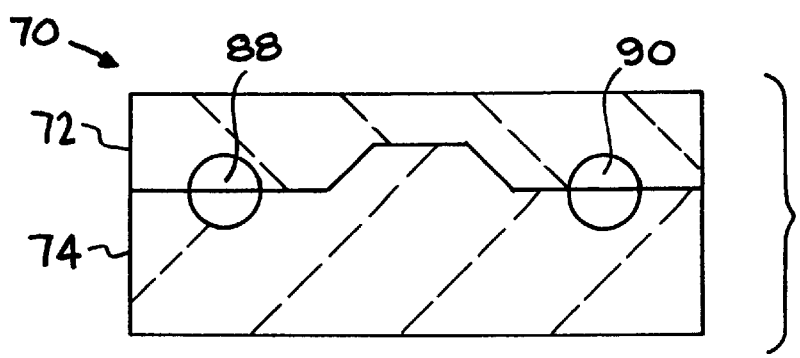

FIGS. 1A–1D show a method of the present invention, referred to herein by the general reference numeral 10, for making a microcapillary with a pair of (100) silicon wafers 12 and 14. An alignment window 16 is anisotropically etched through wafer 12, e.g., with potassium hydroxide (KOH) etching or ethylenediamine pyrocatechol and water (EPW) etching, to precisely match an alignment target 18 that is anisotropically etched as a cavity in the wafer 14. A set of two pairs of matching semicircular microchannels 20, 22, 24 and 26 are isotropically etched into the wafers 12 and 14 on mating bonding surfaces.

In gas chromatography applications where the semicircular microchannels are used to construct cylindrical GC columns, the round cross-sectional geometry is important. It is possible to achieve such well-shaped semicircular cross sections by using the methods described by the present inventors in U.S. Pat. Nos. 5,575,929, issued Nov. 19, 1996. For example, a semicircular microcapillary may be fabricated by depositing boron nitride (BN) or silicon nitride ($Si_3N_4$) on a silicon wafer (e.g., silicon with [100] or [110] crystal orientation). Photolithography is used with a photoresist to create exposed areas in the deposition for plasma etching. A slit entry through to the silicon is created along a path of the ultimate microcapillary. Acetone is used to remove the photoresist. An isotropic etch, e.g., such as $HF/HNO_3/CH_3COOH$, then erodes away the silicon through the trench opening in the deposition layer. A channel with a half-circular cross section is then formed in the silicon along the line of the slit entry in the deposition layer. Wet etching is then used to remove the deposition layer.

A completed structure 30 is formed by bonding the wafers 12 and 14 together using a microscope 32 to observe a precise visual alignment of the alignment target 18 in the alignment window 16. A sticky solution, e.g., photoresist or an adhesive is used to temporarily maintain the alignment for bonding. The bonding, for example, may comprise eutectic, oxide, direct oxide growth, anodic or low-temperature glass bonding. A microcapillary 34 is formed from microchannels 20 and 24, and a microcapillary 36 is formed from microchannels 22 and 26.

FIGS. 2A–2D show a method of the present invention, referred to herein by the general reference numeral 40, for making a microcapillary with a pair of (110) silicon wafers 42 and 44. A fixture 46 has a vertical fitting post 48 formed on it that fits a pair of vertical alignment holes 50 and 52 in wafers 42 and 44. The fitting post 48 and alignment holes are made by anisotropic etching of (110) silicon. A set of two pairs of matching semicircular microchannels 54, 56, 58 and 60 are isotropically etched into the wafers 42 and 44 on mating bonding surfaces. The wafers 42 and 44 are bonded together using the fixture 46 to cam the holes 50 and 52 into precise alignment with one another with the fitting post 48. As before, the bonding may comprise eutectic, oxide, direct oxide growth, anodic or low-temperature glass bonding. A pair of microcapillaries 62 and 64 are thus formed.

FIGS. 3A–3D show a method of the present invention, referred to herein by the general reference numeral 70, for making a microcapillary with a pair of (100) silicon wafers 72 and 74. An alignment hole 76 is anisotropically etched with a slope in wafer 72 to precisely match a similarly sloped alignment post 78 that is anisotropically etched from the wafer 78. For example the slopes are angled at 54.7° by anisotropic etching of (100) silicon. A set of two pairs of matching semicircular microchannels 80, 82, 84 and 86 are isotropically etched into the wafers 72 and 74 on mating bonding surfaces. A completed structure is formed by bonding the wafers 72 and 74 together fitting the post 78 in the hole 76 for a precise physical alignment. The bonding, for example, may comprise eutectic, oxide, direct oxide growth, anodic or low-temperature glass bonding. A microcapillary 88 is formed from microchannels 80 and 84, and a microcapillary 90 is formed from microchannels 82 and 86.

Figure 4A:
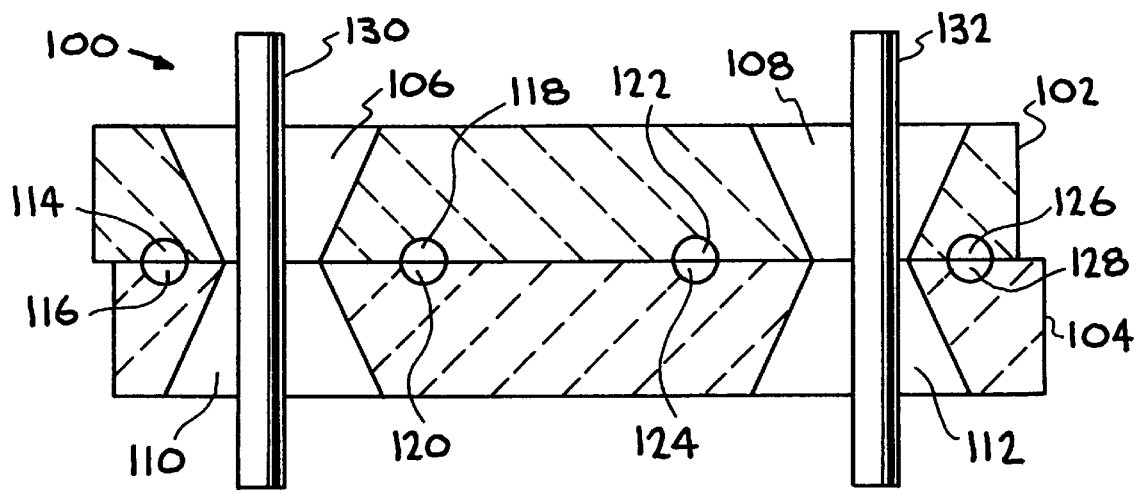
FIGS. 4A and 4B are diagrams of a fourth method embodiment of the present invention for making a microcapillary from two (100) silicon wafers using alignment holes and two pulling posts.
Figure 4B:
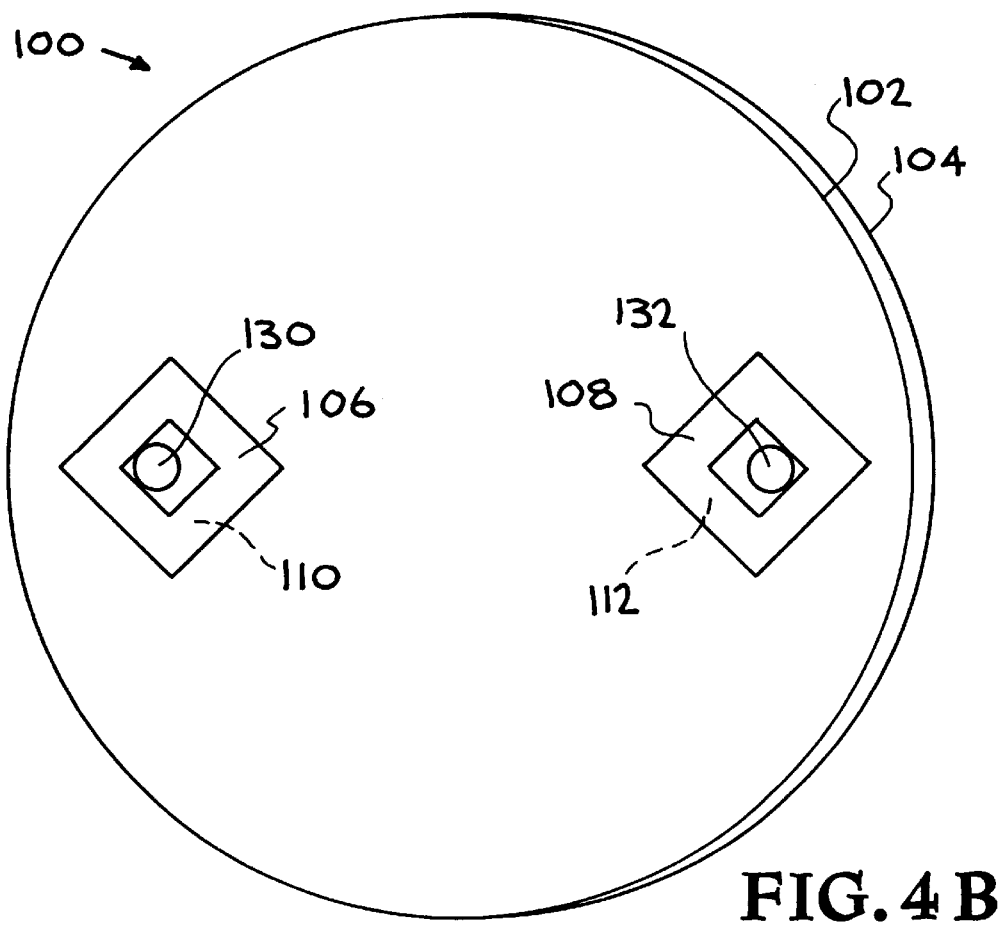

FIGS. 4A and 4B show a method of the present invention, referred to herein by the general reference numeral 100, for making a microcapillary with a pair of (100) silicon wafers 102 and 104. A pair of sloping rectangular or square alignment holes 106 and 108, e.g., angled at 54.7° by anisotropic etching of (100) silicon, are etched into the wafer 102. Another matching pair of sloping rectangular or square alignment holes 110 and 112 are anisotropically etched into the wafer 104. A set of matching pairs of microchannels 114, 116, 118, 120, 122, 124, 126 and 128 are respectively isotropically etched in the wafers 102 and 104 on the sides with the narrow ends of holes 106, 108, 110 and 112. A pair of loose-fitting cylindrical pulling posts 130 and 132 are positioned in the holes 106, 108, 110 and 112 to make a two-point contact with each by pulling the pulling posts 130 and 132 apart. Such action will force the wafers 102 and 104 into microscopic alignment and they can then be bonded together by eutectic, oxide, direct oxide growth, anodic or low-temperature glass bonding. In an alternative embodiment, the silicon wafers 102 and 104 are matched in thickness to ensure the holes 106, 108, 110 and 112 are the same final size.

Figure 5A:
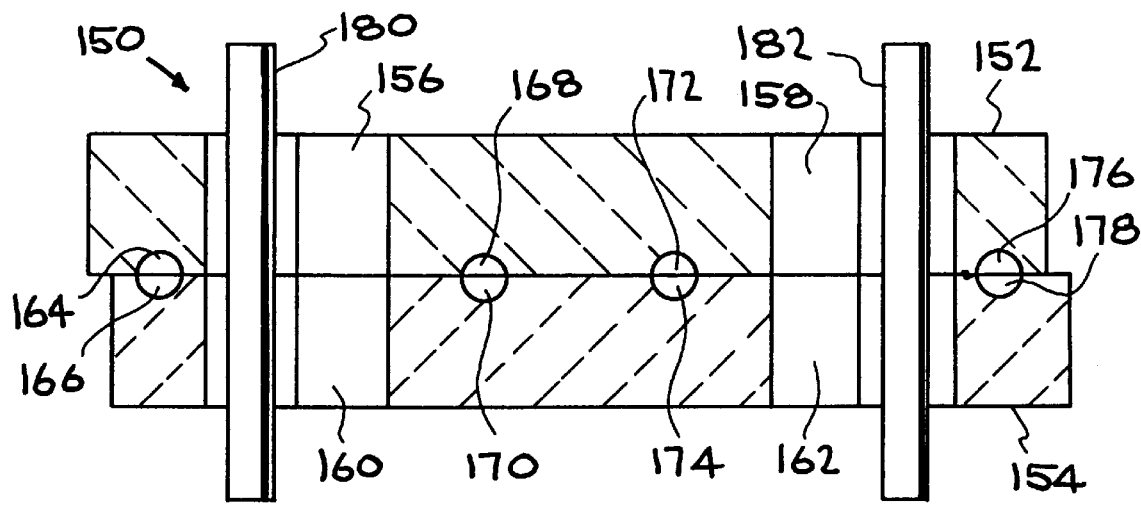
FIGS. 5A and 5B are diagrams of a fifth method embodiment of the present invention for making a microcapillary from two (110) silicon wafers using alignment holes and two pulling posts.
Figure 5B:
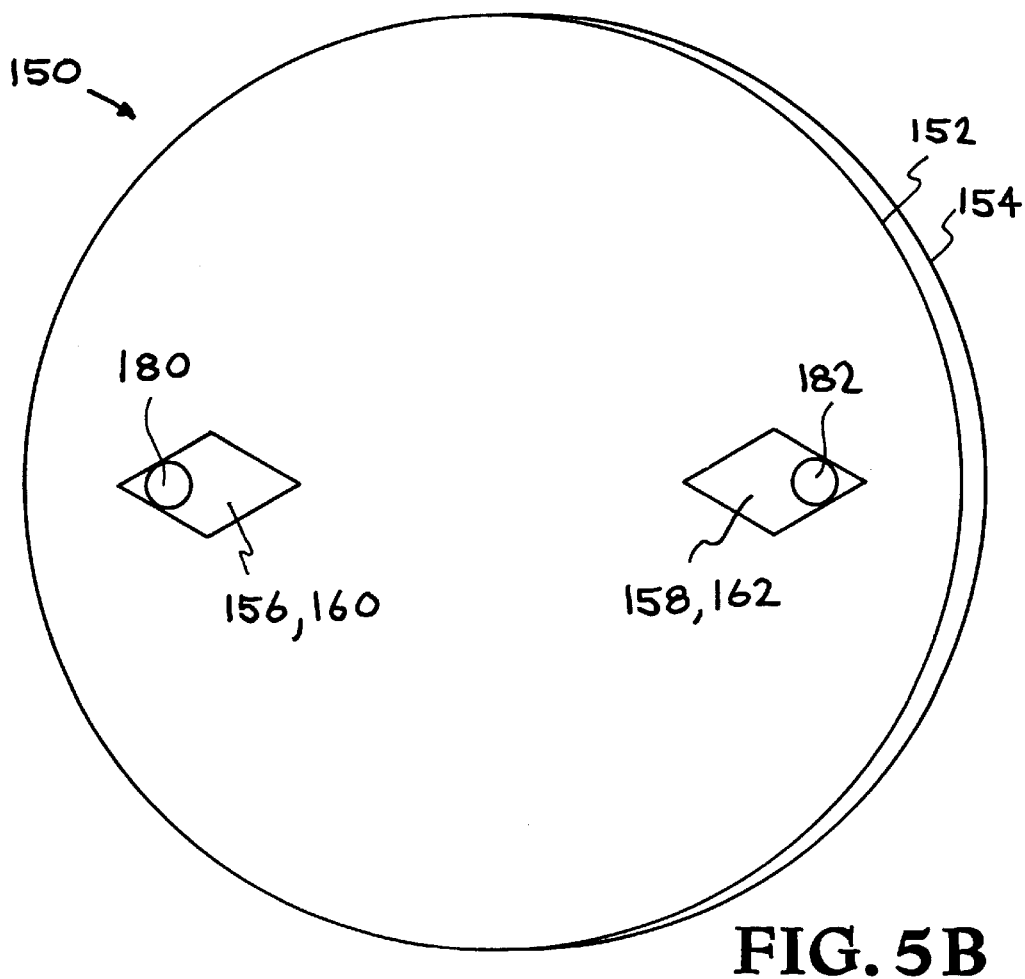

FIGS. 5A and 5B show a method of the present invention, referred to herein by the general reference numeral 150, for making a microcapillary with a pair of (110) silicon wafers 152 and 154. A pair of vertical rhombic alignment holes 156 and 158 are anisotropically etched into the wafer 152. Another matching pair of vertical rhombic alignment holes 160 and 162 are anisotropically etched into the wafer 154. A set of matching pairs of microchannels 164, 166, 168, 170, 172, 174, 176 and 178 are respectively isotropically etched in the wafers 152 and 154. A pair of loose-fitting cylindrical pulling posts 180 and 182 are positioned in the holes 156, 158, 160 and 162 to make a two-point contact with each by pulling the pulling posts 180 and 182 apart. Such action will force the wafers 152 and 154 into microscopic alignment and they can then be bonded together by eutectic, oxide, direct oxide growth, anodic or low-temperature glass bonding.

FIG. 6 illustrates a micro-miniature gas chromatograph column embodiment of the present invention, referred to herein by the general reference numeral 200. The column 200 comprises a matching pair of silicon wafers 202 and 204 in which are respectively etched a complementary pair of half-circular cross-section spiral microcapillaries 206 and 208. When the silicon wafers 202 and 204 are properly joined together, the complementary pair of half-circular cross-section spiral microcapillaries 206 and 208 with form one whole circular cross-section spiral microcapillary. A pair of heating wires 210 and 212 are deposited, e.g., in aluminum, on the outside surfaces of silicon wafers 202 and 204. The area of the heating wires is preferably large enough to be able to quickly heat the whole spiral microcapillary during its use as a column in a gas chromatograph. An exit port 214 is connected to the inner terminus of the whole spiral microcapillary, and an input tube coupling 216 is connected to the outer terminus.

A solid phase material, e.g., very high purity silicone, is loaded into the whole of the spiral microcapillary to complete the fabrication of a separation column. For example, this can be done by mixing very pure quantities of thick viscous silicone and solvent-like liquid chloroform and using the mixture to load a large hypodermic needle 218. A high pressure plunger 220, e.g., a thumbscrew, is used to force the mixture out of the hypodermic needle 218 and down into the input tube coupling 216 and the whole spiral microcapillary (206+208). Once the mixture has completely filled the microcapillary, the hypodermic needle 218 can be disconnected and the chloroform evaporated and flushed out to leave behind just a silicone solid phase.

Although particular embodiments of the present invention have been described and illustrated, such is not intended to limit the invention. Modifications and changes will no doubt become apparent to those skilled in the art, and it is intended that the invention only be limited by the scope of the appended claims.

The invention claimed is:

1. A micro-miniature gas chromatograph separation column, comprising:

a complementary pair of first and second silicon wafers each with matching half-circular parts of a whole spiral microcapillary;

a bond between a respective bonding surface of the first and second silicon wafers for keeping said half-circular parts together; and alignment means etched into the first and second silicon wafers for precision positioning of said half-circular parts, wherein said whole microcapillary has substantially a round cross section.

2. The column of claim 1, wherein:

the alignment means comprises a visual alignment window disposed in the first silicon wafer having a through hole and a corresponding visual alignment target disposed in the second silicon wafer having a depression, wherein said through hole and said depression, when coaxially aligned, visually signal a microscopic alignment of said half-circular parts for bonding of the first and second silicon wafers.

3. The column of claim 1, wherein:

the alignment means comprises a first vertical alignment hole in the first silicon wafer and a corresponding second vertical alignment hole in the second silicon wafer; and a pin simultaneously disposed in said first and second vertical alignment holes for physically-forcing a microscopic alignment of said half-circular parts.

4. The column of claim 1, wherein:

the alignment means comprises an alignment cavity in the first silicon wafer and a corresponding alignment post in the second silicon wafer for physically-forcing a microscopic alignment of said half-circular parts.

5. The column of claim 1, wherein:

the alignment means comprises first and second vertical alignment holes in the first silicon wafer and a corresponding pair of third and fourth vertical alignment holes in the second silicon wafer; and a pair of loose-fitting pins each simultaneously disposed in said first and third vertical alignment holes and said second and fourth alignment holes for physically-forcing a microscopic alignment of said half-circular parts when said pins are pulled apart from one another.

6. The column of claim 5, wherein:

said first through fourth vertical alignment holes are rectangular in plan view and have walls which narrow toward said bonding surfaces; and said pair of loose-fitting pins are each cylindrical in shape, wherein a two-point contact is made with each of said first through fourth vertical alignment holes.

7. The column of claim 1, further comprising:

a heater wire deposited on an outside surface of each of said complementary pair of first and second silicon wafers and providing for electric heating of a solid phase material within said whole spiral microcapillary during operation of a gas chromatograph.

8. The column of claim 1, further comprising:

a silicone solid phase deposited within said whole spiral microcapillary with the aid of liquid chloroform and a hypodermic needle.

9. The column of claim 1, further comprising:

an exit port connected to an inner terminus of said whole spiral microcapillary and disposed near the center of one of the complementary pair of first and second silicon wafers.

10. The column of claim 1, further comprising:

an inlet tube coupling and port connected to an inner terminus of said whole spiral microcapillary and disposed near the center of one of the complementary pair of first and second silicon wafers.

11. A micro-miniature gas chromatograph separation column, comprising:

a complementary pair of first and second silicon wafers each with matching half-circular parts of a whole spiral microcapillary;

a bond between a respective bonding surface of the first and second silicon wafers for keeping said half-circular parts together;

alignment means etched into the first and second silicon wafers for precision positioning of said half-circular parts, wherein said whole microcapillary has substantially a round cross section;

a heater wire deposited on an outside surface of each of said complementary pair of first and second silicon wafers and providing for electric heating of a solid phase material within said whole spiral microcapillary during operation of a gas chromatograph;

a silicone solid phase deposited within said whole spiral microcapillary with the aid of liquid chloroform and a hypodermic needle;

an exit port connected to an inner terminus of said whole spiral microcapillary and disposed near the center of one of the complementary pair of first and second silicon wafers; and an inlet tube coupling and port connected to an inner terminus of said whole spiral microcapillary and disposed near the center of one of the complementary pair of first and second silicon wafers.

* * * * *